US00PP29561P2

(12) United States Plant Patent
Hartman

(10) Patent No.: US PP29,561 P2
(45) Date of Patent: Jul. 31, 2018

(54) ***CALADIUM* PLANT NAMED 'RESTLESS HEART'**

(50) Latin Name: *Caladium X hortulanum*
Varietal Denomination: Restless Heart

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 15/530,467

(22) Filed: Jan. 18, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'Restless Heart', characterized by its intermediate height and upright plant habit; leaf petioles upright to outwardly leaning with development; vigorous growth habit and rapid growth rate; fancy type leaves that are very dark green in color with red-colored venation and interveinal areas that are reddish pink in color with random red orange and green coalescing spots and splotches; and petioles that are tan green and distally, tan pink in color.

4 Drawing Sheets

Botanical designation: *Caladium* X *hortulanum*.
Cultivar denomination: 'RESTLESS HEART'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'Restless Heart'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2010 in Avon Park, Fla. of *Caladium* X *hortulanum* 'Red Flash', not patented, as the female, or seed, parent with *Caladium* X *hortulanum* 'Twist N' Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2011.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2012 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Restless Heart'. These characteristics in combination distinguish 'Restless Heart' as a new and distinct *Caladium* plant:

1. Intermediate in height and upright plant habit; leaf petioles upright to outwardly leaning with development.
2. Vigorous growth habit and rapid growth rate.
3. Fancy type leaves that are very dark green in color with red-colored venation and interveinal areas that are reddish pink in color with random red orange and green coalescing spots and splotches.
4. Petioles that are tan green and distally, tan pink in color.

Plants of the new *Caladium* differ primarily from plants of the female parent, 'Red Flash', in the following characteristics:

1. Plants of the new *Caladium* are shorter than plants of 'Red Flash'.
2. Plants of the new *Caladium* and 'Red Flash' differ in leaf color as leaves of 'Red Flash' have red-colored venation and interveinal areas with pink and white-colored spots and dark green-colored borders.
3. Plants of the new *Caladium* and 'Red Flash' differ in leaf petiole color as leaf petioles of 'Red Flash' are red pink to tan pink in color with darker-colored stipples, stripes and tessellations.

Plants of the new *Caladium* differ primarily from plants of the male parent, 'Twist N' Shout', in the following characteristics:

1. Plants of the new *Caladium* are denser than plants of 'Twist N' Shout'.
2. Plants of the new *Caladium* and 'Twist N' Shout' differ in leaf color as leaves of 'Twist N' Shout' are olive green in color with green to coppery bronze-colored venation and coppery orange-colored spots and blotches.

3. Plants of the new *Caladium* and 'Twist N' Shout' differ in leaf petiole color as leaf petioles of 'Twist N' Shout' are green in color.

Plants of the new *Caladium* can be compared to plants of *Caladium* X *hortulanum* 'Frieda Hemple', not patented. In side-by-side comparisons, plants of the new *Caladium* differ primarily from plants of 'Frieda Hemple' in the following characteristics:

1. Plants of the new *Caladium* and 'Frieda Hemple' differ in leaf color as leaves of 'Frieda Hemple' are medium green in color with bright red-colored centers and venation.
2. Plants of the new *Caladium* and 'Frieda Hemple' differ in leaf petiole color as leaf petioles of 'Frieda Hemple' appear to be almost black in color.

Plants of the new *Caladium* can be compared to plants of *Caladium* X *hortulanum* 'Postman Joyner', not patented. In side-by-side comparisons, plants of the new *Caladium* differ primarily from plants of 'Postman Joyner' in the following characteristics:

1. Plants of the new *Caladium* and 'Postman Joyner' differ in leaf color as leaves of 'Postman Joyner' are dark green in color with bright red-colored centers.
2. Plants of the new *Caladium* and 'Postman Joyner' differ in leaf petiole color as leaf petioles of 'Postman Joyner' are dark olive green and dark brown appearing to be almost black in color.

Plants of the new *Caladium* can be compared to plants of *Caladium* X *hortulanum* 'Freckles', disclosed in U.S. Plant Pat. No. 27,943. In side-by-side comparisons, plants of the new *Caladium* differ primarily from plants of 'Freckles' in leaf color as leaves of plants of 'Freckles' are dark green in color with orange and pink-colored spots and blotches.

Plants of the new *Caladium* can also be compared to plants of *Caladium* X *hortulanum* 'Burning Heart', disclosed in U.S. Plant Pat. No. 27,071. In side-by-side comparisons, plants of the new *Caladium* differ primarily from plants of 'Burning Heart' in leaf color as leaves of plants of 'Burning Heart' are bronze in color with contrasting salmon orange-colored spots.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Restless Heart' in a container and grown in a shadehouse (tuber not de-eyed).

The photograph at the top of the second sheet is a comparison view of typical potted plants of the female parent, 'Red Flash' (right), 'Restless Heart' (center) and the male parent, 'Twist N' Shout' (left).

The photograph at the bottom of the second sheet is a comparison view of typical potted plants of 'Frieda Hemple' (left), 'Restless Heart' (center) and 'Postman Joyner' (right).

The photograph at the top of the third sheet is a side perspective view of typical plants of 'Restless Heart' grown in an open field.

The photograph at the bottom of the third sheet is a close-up view of typical freshly-harvested tubers with roots and leaf petioles of 'Restless Heart'.

The photograph at the top of the fourth sheet is a comparison view of typical plants of 'Restless Heart' grown in containers; the plant on the left has not had its tuber de-eyed and the plant on the right has had its tuber de-eyed prior to planting.

The photograph at the bottom of the fourth sheet is a close-up view of a typical inflorescence of 'Restless Heart'.

DETAILED BOTANICAL DESCRIPTION

The aforementioned photographs and following observations and measurements describe plants grown in 15-cm containers in a polypropylene-covered shadehouse (50% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were seven weeks old and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium* X *hortulanum* 'Restless Heart'.

Parentage:

*Female, or seed, parent.*—*Caladium* X *hortulanum* 'Red Flash', not patented.

*Male, or pollen, parent.*—*Caladium* X *hortulanum* 'Twist N' Shout', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments irregularly elliptic to ovate in shape. Height: About 2.7 cm. Diameter: About 3.3 cm to 5.8 cm. Segment height: About 1.5 cm to 2 cm. Segment diameter: About 2 cm. Texture: Thick, starchy; somewhat brittle. Color: Epidermis, freshly-harvested: Close to 199B and N199B. Epidermis, dried: Close to 200A to 200B. Cortical tissue: Close to 1D and 2D. Axillary buds: Close to N155C. Root description: Thick, fleshy contractile roots with few lateral branches; color, close to N155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate in height and upright plant habit; vigorous growth habit and rapid growth rate; potted plants in finished or saleable form in about seven weeks after planting tubers; leaf petioles and leaves arise from one or more growing points on tubers; petioles mostly upright and outwardly leaning with development; inflorescences held at the foliar plane on strong upright scapes.

*Plant height, from soil level to top of foliar plane, shadehouse-grown potted plants*.—About 29 cm to 33 cm.

*Plant height, from soil level to top of inflorescences, shadehouse-grown potted plants*.—About 34.5 cm.

*Plant diameter or spread, shadehouse-grown potted plants*.—About 38 cm to 40 cm.

*Number of shoots per plant, shadehouse-grown potted plants, tubers not de-eyed*.—About one to two develop per #1 tuber.

*Number of shoots per plant, shadehouse-grown potted plants, tubers de-eyed*.—About three to four develop per #1 tuber.

*Cataphylls, shadehouse-grown potted plants*.—Length: About 6 cm to 10.3 cm. Width: About 1.2 cm to 1.6 cm. Shape: Deltoid. Apex: Acute to acuminate. Base: Sheathing the stem. Color, inner surface: Close to N155C; colors and patterns on the outer surface are visible on the inner surface. Color, outer surface: Close to N170D tinged with close to 182C and 182D; streaked and stippled with close to 195A tinged with close to 177D, with development, color becoming closer to 199B.

Leaf description:

*Arrangement and type*.—Alternate; simple; fancy type.

*Length, shadehouse-grown potted plants*.—About 18.4 cm to 24.3 cm.

*Width, shadehouse-grown potted plants*.—About 13.2 cm to 17.6 cm; when flattened, about 13.8 cm to 18 cm.

*Shape*.—Ovate.

*Apex*.—Acute or cuspidate.

*Base*.—Sagittate to peltate.

*Margin*.—Entire; wavy with broad undulations.

*Texture, upper and lower surfaces*.—Smooth, glabrous.

*Luster, upper surface*.—Dull sheen.

*Luster, lower surface*.—Glaucous, dull sheen.

*Venation pattern*.—Pinnate.

*Color, shadehouse-grown potted plants*.—Developing and fully expanded leaves, upper surface: Background color: Close to 147A tinged with close to 139A or close to 147A tinged with close to 183C. Margins: Close to 147A tinged with close to 139A or close to 147A tinged with close to 183C. Basal notch: Close to 53B and 187C. Midvein and primary venation: Close to 53B tinged with close to 53A. Areas surrounding venation: Close to 53B. Interveinal areas: Close to 53B. Random spots and splotches: Close to 47A, close to 47A tinged with close to 181B, or close to 147A tinged with close to 139A or close to 147A tinged with close to 183B to 183C. Developing and fully expanded leaves, lower surface: Background color: Close to 191A. Margins: Close to 191A. Basal notch: Close to 187C. Midvein: Close to 185B streaked with close to 185A. Primary venation: Close to 185B. Leaf center and areas surrounding venation: Close to 185B or darker than 185B. Interveinal areas: Random sectors, close to N170C tinged with close to 182D or close to 191A.

*Petioles*.—Aspect: Initially upright and straight; with development, somewhat outwardly leaning; flexible. Length, shadehouse-grown potted plants: About 19 cm to 23.2 cm. Diameter, distally, shadehouse-grown potted plants: About 3.5 mm to 5 mm. Diameter, proximally, shadehouse-grown potted plants: About 7 mm to 11 mm. Texture: Smooth, glabrous. Color, shadehouse-grown potted plants: Close to 147B with areas flushed with close to 182D and faintly streaked, stippled and tessellated with close to 177D; proximally, close to 148C and 148D tinged with close to 147B and faintly streaked, stippled and tessellated with close to 147B; below the leaf and petiole junction, close to 51C to 51D and 49C variably tinged with close to 147D and streaked and stippled with close to 185B. Wing length, shadehouse-grown potted plants: About 3.3 cm to 4.2 cm. Wing diameter, shadehouse-grown potted plants: About 6 mm. Texture and luster, inner and outer surfaces: Smooth, glabrous; dull. Wing color, shadehouse-grown potted plants: Inner surface: Close to N155C; colors and patterns on the outer surface are visible on the inner surface. Outer surface: Close to 196C tinged with close to N170D and 148B, streaked and stippled with close to 147A and tinged with close to 200C.

Inflorescence description: Inflorescences observed on seven week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; jasmine-like with camphor note.

*Natural flowering season and flower longevity*.—Plants of the new *Caladium* typically flower during the spring in central Florida; flowers develop about seven weeks after growth commences; inflorescences last about three days before fading; inflorescences persistent.

*Spathe*.—Length, overall: About 12.5 cm. Length, distal open portion: About 8.3 cm. Length, proximal closed portion: About 4.2 cm. Width, distal open portion: About 5.4 cm. Depth, distal open portion: About 2.5 cm. Width, at constriction: About 1.35 cm. Width, proximal closed portion: About 2.6 cm. Shape, open portion: Elliptic. Apex: Acute to acuminate. Base: Obtuse. Margin: Entire; smooth or slightly reflexed. Texture, front and rear surfaces: Smooth, glabrous. Luster, front surface: Dull sheen. Luster, rear surface: Dull sheen; proximally, slightly glaucous. Color, front surface: Distal open portion:

Close to 155C with sparse and fine speckles, close to 183B and 183C; with development, color becoming closer to 199B. Proximal closed portion: Close to 194A; towards the base, darkly flushed with close to 187A; color does not change with development. Color, rear surface: Distal open portion: Close to 155B; center, flushed with close to 145C to 145D; color does not change with development. Proximal closed portion: Close to 147B and 147C with diffuse mottling and flecks, close to 183C and 187B; color does not change with development.

*Spadix*.—Length, overall: About 9.4 cm. Length, male flower zone: About 6.3 cm. Length, sterile zone: About 1.3 cm. Length, female flower zone: About 1.8 cm. Diameter, male flower zone: About 9 mm. Diameter, sterile flower zone: About 6 mm. Diameter, female flower zone: About 8 mm. Shape: Columnar, spindle-shaped. Apex: Acute. Base: Obtuse. Aspect: Upright. Color, mature, male zone: Close to 11D. Color, mature, sterile zone: Close to 158D. Color, mature, female zone: Close to 158C. Male flowers: Quantity per spadix: About 160. Shape: Obovate. Height: About 3 mm. Diameter: About 2.8 mm. Pollen amount: Moderate. Pollen color: Close to 9D. Female flowers: Quantity per spadix: About 158. Shape: Obovate. Height: About 2 mm. Diameter: About 2 mm. Stigma color: Close to 158C. Ovary color: Close to 158C.

*Scape*.—Length: About 22 cm. Diameter: About 5.8 mm. Strength: Sturdy; flexible. Aspect: Mostly erect. Texture and luster: Smooth, glabrous; dull sheen; distally, glaucous. Color: Close to 147B with areas flushed with close to 182D and faintly streaked, stippled and tessellated with close to 177D; towards the base, close to 148C and 148D tinged with close to 147B and faintly streaked, stippled and tessellated with close to 147B; just below spathe, close to 147D tinged with close to 51C to 51D and 49C and streaked and stippled with close to 185B.

*Seeds and fruits*.—To date, seed and fruit development have not been observed on plants of the new *Caladium*.

Disease & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Restless Heart' as illustrated and described.

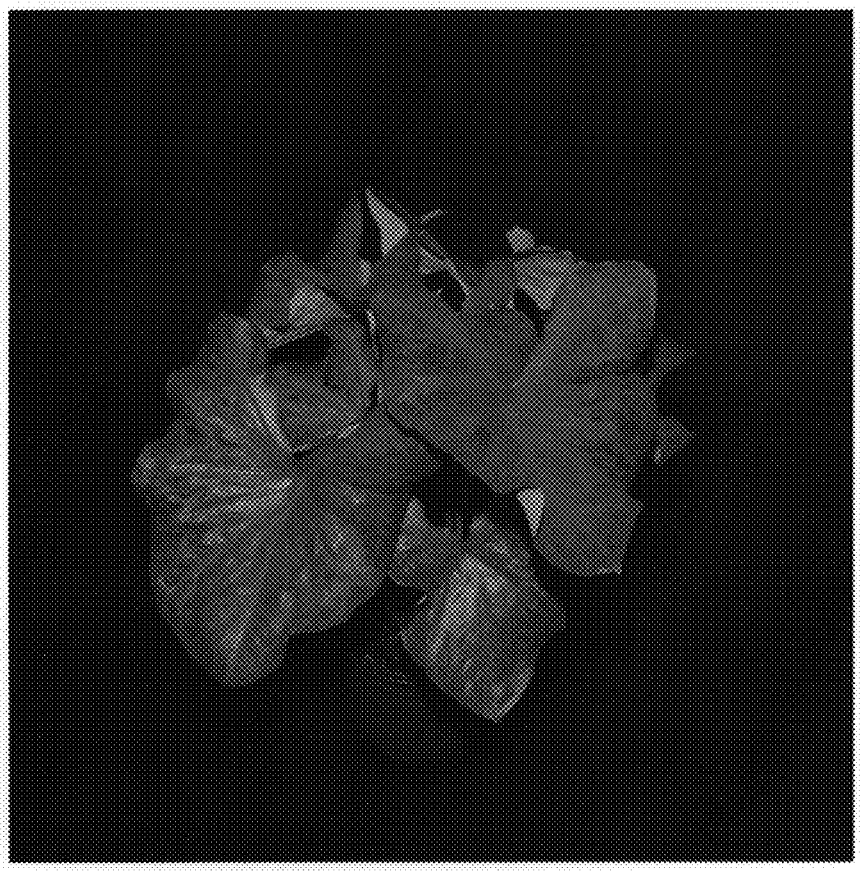

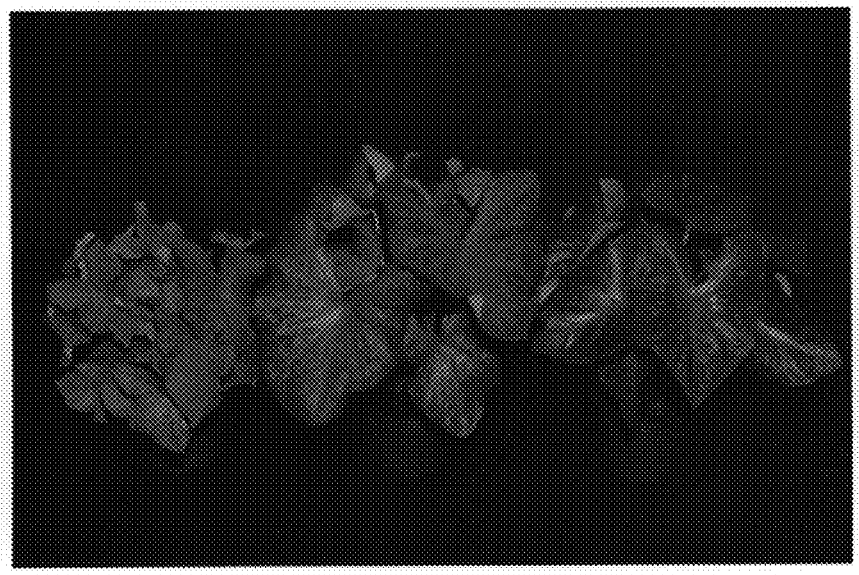
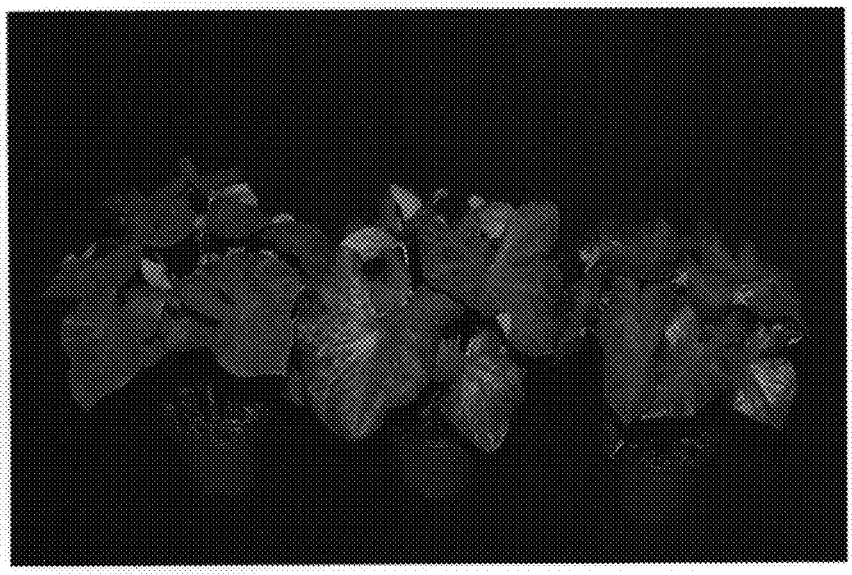

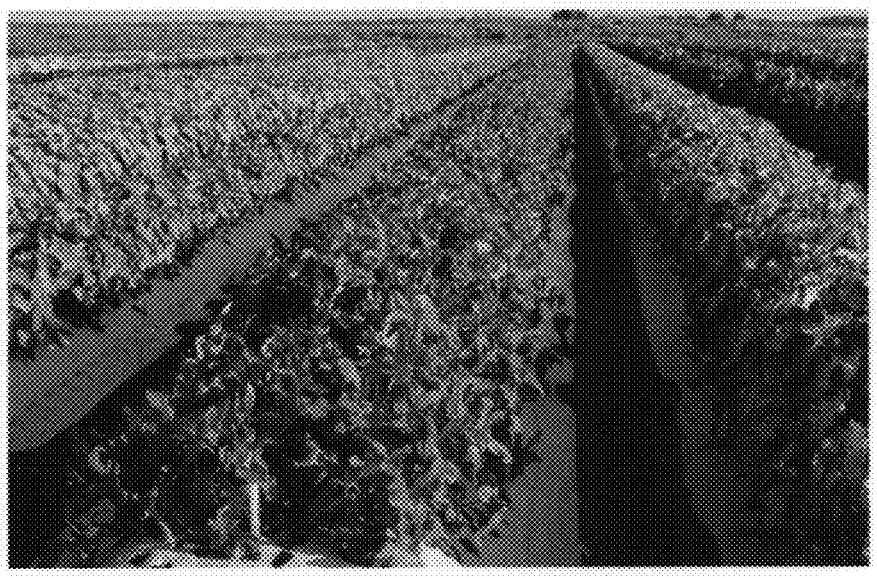
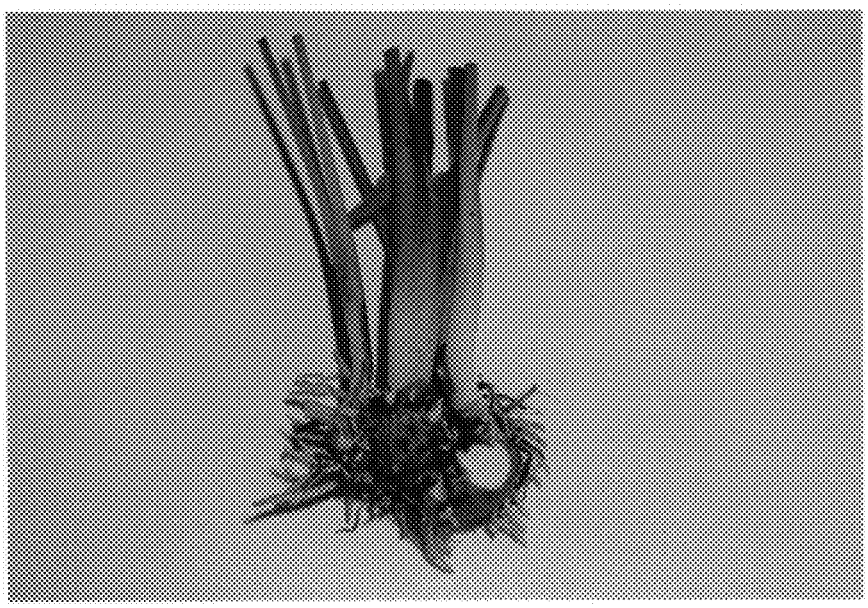

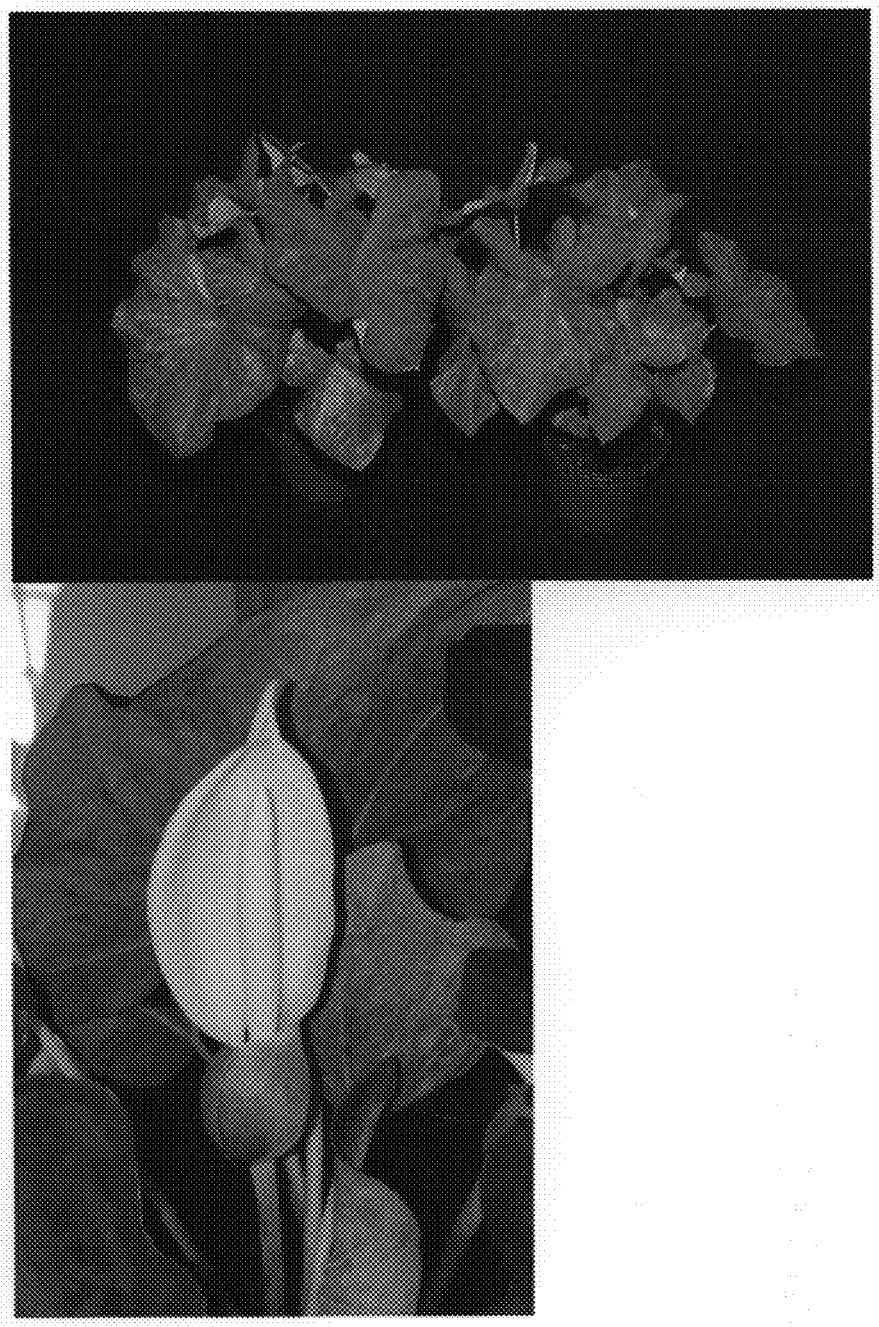

* * * * *